US006479474B2

(12) United States Patent
DeLuca et al.

(10) Patent No.: US 6,479,474 B2
(45) Date of Patent: *Nov. 12, 2002

(54) DIETARY CALCIUM AS A SUPPLEMENT TO VITAMIN D COMPOUND TREATMENT OF MULTIPLE SCLEROSIS

(75) Inventors: Hector F. DeLuca, Deerfield; Margherite T. Cantorna, Middleton; Jean Humpal-Winter, Poynett, all of WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/349,528

(22) Filed: Jul. 8, 1999

(65) Prior Publication Data

US 2002/0016313 A1 Feb. 7, 2002

(51) Int. Cl.$^7$ .......................... A61K 31/59; A61K 33/10
(52) U.S. Cl. ........................................ 514/167; 424/687
(58) Field of Search ........................... 514/167; 424/687

(56) References Cited

U.S. PATENT DOCUMENTS

| | | | |
|---|---|---|---|
| 4,279,826 A | 7/1981 | DeLuca et al. | |
| 4,307,025 A | 12/1981 | DeLuca et al. | |
| 4,448,721 A | 5/1984 | DeLuca et al. | |
| 4,500,460 A | 2/1985 | DeLuca et al. | |
| 4,502,991 A | 3/1985 | DeLuca et al. | |
| 4,505,906 A | 3/1985 | DeLuca et al. | |
| 4,552,698 A | 11/1985 | DeLuca et al. | |
| 4,588,528 A | 5/1986 | DeLuca et al. | |
| 4,594,192 A | 6/1986 | DeLuca et al. | |
| 4,619,920 A | 10/1986 | DeLuca et al. | |
| 4,698,328 A | * 10/1987 | Neer et al. ..................... | 514/12 |
| 4,769,181 A | 9/1988 | DeLuca et al. | |
| 4,973,584 A | 11/1990 | DeLuca et al. | |
| 5,030,772 A | 7/1991 | DeLuca et al. | |
| 5,036,061 A | 7/1991 | DeLuca et al. | |
| 5,237,110 A | 8/1993 | DeLuca et al. | |
| 5,260,199 A | 11/1993 | DeLuca et al. | |
| 5,260,290 A | 11/1993 | DeLuca et al. | |
| 5,328,903 A | 7/1994 | DeLuca et al. | |
| 5,371,249 A | 12/1994 | DeLuca et al. | |
| 5,373,004 A | 12/1994 | DeLuca et al. | |
| 5,380,720 A | 1/1995 | DeLuca et al. | |
| 5,395,830 A | 3/1995 | DeLuca et al. | |
| 5,397,775 A | 3/1995 | DeLuca et al. | |
| 5,414,098 A | 5/1995 | DeLuca et al. | |
| 5,716,946 A | 2/1998 | DeLuca et al. ............. | 514/167 |

FOREIGN PATENT DOCUMENTS

| | | |
|---|---|---|
| CA | 2096196 | 5/1993 |
| EP | 0 579 915 A1 | 5/1993 |
| EP | 0 702 954 A2 | 3/1996 |
| EP | 0 580 968 B1 | 8/1996 |
| JP | 63104926 | 5/1988 |
| WO | WO 92/21355 | 12/1992 |
| WO | WO 95/01960 | 1/1995 |
| WO | WO 98/40085 | 9/1998 |
| WO | WO 93/51678 | 11/1998 |
| WO | WO 98/49138 | 11/1998 |
| WO | WO 00/66098 | 11/2000 |

OTHER PUBLICATIONS

Goldberg, "Multiple sclerosis. Vitamin D and calcium as environmental determinants of prevalence. 2. Biochemical genetic factors" Int. J. Environ. Stud. (1974), 6(2–3), 121–9 Coden: IJEVAW. (1974).*

M.T. Cantorna, et al., "1,25–Dihydroxyvitamin $D_3$ Reversibly Blocks the Progression of Relapsing Encephalomyelitis, a Model of Multiple Sclerosis," Proc. Natl. Acad. Sci. USA 93: 7861–7864, 1996.

J.–F. Bach, "Immunosuppressive therapy of autoimmune diseases," Immun. Today 14 (6) :322–326, 1993.

Bhalla, Ashok K., et al., "1,25–Dihydroxyvitamin $D_3$ Inhibits Antigen–Induced T Cell Activation," J. Immunol.,1984, 133:1748–54.

Branisteanu, D., et al., "Prevention of murine experimental allergic encephalomyelitis: cooperative effects of cyclosporine and $1\alpha25-(OH)_2D_3$, " J. Neuroimmun. 61(199):151–160, 1995.

S. Brocke, et al., "Infection and multiple sclerosis: a possible role for superantigens?" Trends in Microbiol. 2(7) 250–254, 1994.

Cantorna, M., et al., "1,25–Dihydroxyvitamin $D_3$ reversibly blocks the progression of relapsing encephalomyelitis, a model of multiple sclerosis," Proc. Natl. Acad. Sci. USA 93:7861–7864, 1996.

Ebers, George C., et al., "A Population–Based Study of Multiple Sclerosis in Twins," N. Engl. J. Med., 1986; 315:1638–42.

Ebers, George C., et al., "A full genome search in multiple sclerosis, " Nature Genet., 1996, 13:472–76.

Haines, J.L., et al. (The Multiple Sclerosis Genetics Group), "A complete genomic screen for multiple sclerosis underscores a role for the major histocompatability complex, " Nature Genet.,1996, 13:469–71.

Lacey, David L., et al., "Vitamin D Affects Proliferation of a Murine T Helper Cell Clone," J. Immunol., 1987, 138:1680–86.

(List continued on next page.)

Primary Examiner—Theodore J. Criares
Assistant Examiner—Jennifer Kim
(74) Attorney, Agent, or Firm—Quarles & Brady LLP (57) ABSTRACT

A method of and composition for diminishing multiple sclerosis symptoms are disclosed. In one embodiment, the method comprises the step of administrating an amount of calcium and a vitamin D compound effect to diminish multiple sclerosis symptoms. In another embodiment, the invention is a pharmaceutical composition comprising an amount of calcium and vitamin D compound effective to diminish multiple sclerosis symptoms.

2 Claims, 6 Drawing Sheets

OTHER PUBLICATIONS

Lemire, Jacques M., et al., "1α, 25–Dihydroxyvitamin $D_3$ Supresses Proliferation and Immunoglobulin Production by Normal Human Peripheral Blood Mononuclear Cells, " *J. Clin. Invest.*, 1984, 74:657–61.

Lemire, J., et al., "1,25–Dihydroxyvitamin $D_3$ Prevents the In Vivo Induction of Murine Experimental Autoimmune Encephalomyelitis," *J. Clin. Invest.* 87:1103–1107, 1991.

Miller, S.D., and Karpus, W.J., "The immunopathogenesis and regulation of T–cell–mediated demyelinating diseases," *Immun. Today* 15(8) :356–361, 1994.

Müller, K., and Bendtzen, K., "Inhibition of Human T Lymphocyte Proliferation and Cytokine Production by 1,25–Dihydroxyvitamin $D_3$ Differential Effects on CD45RA+ and CD45RO+ Cells, "*Autoimmunity*, 14:37–43 (1992).

Nataf, S., et al., "1,25–Dihydroxyvitamin $D_3$ Exerts Regional Effects in the Central Nervous System during Experimental Allergic Encephalomyelitis," *J. Neuropath. Exp. Neurol.* 55(8) :904–914, 1996.

Rigby, William F.C., et al., "Inhbition of T Lymphocyte Mitogenesis by 1,25–Dihydroxyvitamin $D_3$ (Calcitriol)," *J. Clin. Invest.*, 1984, 74:1451–55.

R. A. Rudick and D. E. Goodkin, "Measuring Impairment and Disability," *Treatment of Multiple Sclerosis: Trial Design, Results, and Future Perspectives,* Springer–Verlag, London, pp. 48–53, 1992.

Saporito, M., et al., "Chronic 1,25–dihydroxyvitamin $D_3$–mediated induction of nerve growth factor mRNA and protein in L929 fibroblasts and in adult rat brain," *Brain Res.* 633:189–196, 1994.

Sawcer, Stephen, et al., "A genome screen in multiple sclerosis reveals susceptibility loci on chromosome 6p21 and 17q22," *Nature Genet.*, 1996, 13:464–68.

L. Steinman, "Escape from 'Horror Autotoxicus': Pathogenesis and Treatment of Autoimmune Disease," *Cell* 80:7–10, 1995.

Tweedie, D., "Vitamin Treatment of Hemiplegia," *Med. J. Malaysia* 33(2) :193–194, 1978.

\* cited by examiner

DIETARY CALCIUM AS A SUPPLEMENT TO VITAMIN D COMPOUND TREATMENT OF MULTIPLE SCLEROSIS

CROSS-REFERENCE TO RELATED APPLICATION

STATEMENT REGARDING FEDERALLY SPONSORED RESEARCH OR DEVELOPMENT

BACKGROUND OF THE INVENTION

Vitamin D is a recent arrival in the roster of agents that are known to regulate the immune system. Vitamin D is converted in a two-step process to the hormone, 1,25-dihydroxycholecalciferol $(1,25\text{-}(OH)_2D_3)^1$ that is a key factor in regulating serum calcium, phosphorus and bone (DeLuca, 1997). This hormone acts in a steroid hormone-like mechanism through a nuclear receptor, the vitamin D receptor (VDR), which is a member of the steroid hormone receptor superfamily (Pike, 1991; Ross, et al., 1993). The discovery of VDR in peripheral blood lymphocytes (Bhalla, et al., 1983; Provvedini, et al., 1983) is a factor that led to the realization that $1,25\text{-}(OH)_2D_3$ is a significant regulator of the immune system. The most striking evidence of a role for $1,25\text{-}(OH)_2D_3$ as an immune system regulator comes from in vivo experiments. $1,25\text{-}(OH)_2D_3$ can prevent the development of EAE (Cantorna, et al., 1996 and U.S. Pat. No. 5,716,946; Lemire and Archer, 1991), experimental arthritis (Cantorna, et al., 1998a), and $1,25\text{-}(OH)_2D_3$ can markedly inhibit transplant rejection (Bouillon, et al., 1995; Hullett, et al., 1998).

[1] Abbreviations: central nervous system, CNS; 1,25-dihydroxycholecalciferol, $1,25\text{-}(OH)_2D_3$; experimental autoimmune encephalomyelitis, EAE; glyceraldehyde-3-phosphate dehydrogenase, lymph node, LN; multiple sclerosis, MS; interferon γ, IFN-γ; interleukin-4, IL-4; transforming growth factor β1, TGF-β1; tumor necrosis factor-α, TNF-α; type-1 helper, Th1; type-2 helper, Th2; vitamin D receptor, VDR.

EAE is mediated by CD4+ T cells, which mount an inappropriate immune-mediated attack on the central nervous system (CNS). Type-1 helper (Th1) cells specific for CNS antigens induce the disease and the Th1 cytokines interferon (IFN)-γ and tumor necrosis factor (TNF)-α are associated with EAE in mice (Holda and Swanborg, 1982; Powell, et al., 1990). Conversely, type-2 helper (Th2) cells and other cell types which produce interleukin (IL)-4 and transforming growth factor (TGF)-β1 in response to CNS antigens are known to ameliorate EAE. In vivo $1,25\text{-}(OH)_2D_3$ treatments result in a net loss in the total number of lymphocytes and a net increase in the expression of IL-4 and TGF-β1 (Cantorna, et al., 1998b). Conversely the in vivo 1,25-treatments had no effect on IFN-γ or TNF-α expression (Cantorna, et al., 1998b). The role, if any, for calcium in the regulation of the immune response remains unclear.

BRIEF SUMMARY OF THE INVENTION

The present invention is a method of more effectively treating multiple sclerosis patients. The method comprises the step of administration of an amount of calcium that renders a vitamin D compound effective in preventing or markedly reducing MS symptoms. Preferably, this amount of calcium is 0.5–2 g per patient per day. Most preferably, the amount is between 1 and 2 g of calcium as a salt with a variety of anions, e.g. $CO_3^-$, $PO_4^-$, $Cl_2^-$ acetate, gluconate, citrate, etc.

In one embodiment, the vitamin D compound is 1α,25-dihydroxyvitamin $D_3$ $(1,25\text{-}(OH)_2D_3)$, 19-nor-1,25-dihydroxyvitamin $D_2$ (19-nor-1,25-$(OH)_2D_3$), 24-homo-22-dehydro-22E-1α,25-dihydroxyvitamin $D_3$ (24-homo-22-dehydro-22E-1,25-$(OH)_2D_3$), 1,25-dihydroxy-24(E)-dehydro-24-homo-vitamin $D_3$ $(1,25\text{-}(OH)_2$-24-homo $D_3)$, or 19-nor-1,25-dihydroxy-21-epi-vitamin $D_3$ (19-nor-1,25-$(OH)_2$-21-epi-$D_3$). In a most preferred form of the invention, the compound used is $1,25(OH)_2D_3$.

In another embodiment, the present invention is a pharmaceutical composition comprising an amount of vitamin D and an amount of calcium that renders the vitamin D compound more effective in reducing the multiple sclerosis symptoms.

It is an object of the present invention to more effectively diminish multiple sclerosis symptoms in a multiple sclerosis patient.

It is another object of the present invention to reduce the amount of vitamin D compound needed to alleviate MS symptoms.

Other features, advantages and objects of the present invention will become apparent to one of skill in the art after review of the specification, claims and drawings.

DETAILED DESCRIPTION OF THE INVENTION

The active form of vitamin D (1,25-dihydroxycholecalciferol) is a potent immune system regulator. We have discovered that treating B10.PL mice with 1,25-dihydroxycholecalciferol and feeding the mice diets high in calcium can completely suppress the induction of experimental autoimmune diseases, such as experimental autoimmune encephalomyelitis (EAE). Because B10.PL mice are an accepted experimental model for multiple sclerosis, we believe these results indicate that one could more effectively treat multiple sclerosis patients by treating the patients with a vitamin D compound together with a calcium supplement. We believe that this combination would more effectively treat multiple sclerosis than treatment by vitamin D compounds alone, such as that treatment described in U.S. Pat. No. 5,716,946, DeLuca, et al. (incorporated by reference).

Therefore, in one embodiment, the present invention is a method of treating human multiple sclerosis patients by administering an amount of calcium that will allow a vitamin D compound, preferably 1,25(OH)$_2$D$_3$ or analogs thereof, to more effectively diminish specific multiple sclerosis symptoms. The method comprises selecting a multiple sclerosis patient and administering a calcium supplement and sufficient amount of the vitamin D analog to the patient such that the multiple sclerosis symptoms are abated.

In a particularly advantageous form of the reaction, the administered compound is either 1α,25-dihydroxyvitamin D$_3$ (1,25-(OH)$_2$D$_3$), 19-nor-1,25-dihydroxyvitamin D$_2$ (19-nor-1,25-(OH)$_2$D$_3$), 24-homo-22-dehydro-22E-1α,25-dihydroxyvitamin D$_3$ (24-homo-22-dehydro-22E-1,25-(OH)$_2$D$_3$), 1,25-dihydroxy-24(E)-dehydro-24-homo-vitamin D$_3$ (1,25-(OH)$_2$-24-homo D$_3$), 19-nor-1,25-dihydroxy-21-epi-vitamin D$_3$ (19-nor-1,25-(OH)$_2$-21-epi-D$_3$), 1αhydroxy vitamin D$_3$ or 1α hydroxy vitamin D$_2$.

In another form of the present invention, the vitamin D compound has the formula wherein $X^1$ and $X^2$ are each selected from the group consisting of hydrogen and acyl; wherein $Y^1$ and $Y^2$ can be H, or one can be O-aryl, O-aryl, alkyl of 1–4 carbons, taken together to form an alkene having the structure of $B_1$ where $B_1$ and $B_2$ can be selected from the group consisting of H, alkyl of 1–4 carbons and aryl, and can have a β or α configuration; $Z^1=Z^2=$H or $Z^1$ and $Z^2$ together are $=CH_2$; and wherein R is an alkyl, hydroxyalkyl or fluoroalkyl group, or R may represent the following side chain:

wherein (a) may have an S or R configuration, $R^1$ represents hydrogen, hydroxy or O-acyl, $R^2$ and $R^3$ are each selected from the group consisting of alkyl, hydroxyalkyl and fluoroalkyl, or, when taken together represent the group -(CH$_2$)$_m$- wherein m is an integer having a value of from 2 to 5, $R^4$ is selected from the group consisting of hydrogen, hydroxy, fluorine, O-acyl, alkyl, hydroxyalkyl and fluoroalkyl, wherein if $R^5$ is hydroxyl or fluoro, $R^4$ must be hydrogen or alkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon-carbon double bond, $R^8$ may be H or CH$_3$, and wherein n is an integer having a value of from 1 to 5, and wherein the carbon at any one of positions 20, 22, or 23 in the side chain may be replaced by an O, S, or N atom.

U.S. Pat. No. 5,716,946 (DeLuca, et al., Issued Feb. 10, 1998) describes treatment of multiple sclerosis with vitamin D compounds. One would preferably design a treatment schedule using the description of vitamin D treatment disclosed in this patent. In the method of the present invention, one would supplement this treatment with administration of a calcium compound, preferably selected from calcium carbonate, calcium acetate, calcium gluconate, calcium hydrogen phosphate, calcium phosphate and calcium citrate. Preferred are calcium carbonate, calcium acetate and calcium citrate.

Preferably, one will supplement the vitamin D compound treatment with between 0.5 and 2 g of calcium per day per human patient (typically 160 pound patient). Most preferably, administration will be simultaneous with vitamin D compound administration, although simultaneous administration is not required.

The present invention is also a pharmaceutical composition comprising an amount of vitamin D compound effective to diminish multiple sclerosis symptoms and an amount of calcium effective to enhance the effects of the vitamin D compound administration. Preferably, the dose of vitamin D compound is between 0.25 μg and 10 μg and the dose of calcium is between 0.5 and 2 g. The pharmaceutical composition additionally comprises a pharmaceutically acceptable carrier.

EXAMPLES

Experiments described below use mice induced to develop EAE and fed diets with various amounts of calcium and 1,25-dihydroxyvitamin D$_3$. Parameters measured include EAE development and severity, serum calcium, weight, total cell numbers in the lymph node, interleukin-4 and transforming growth factor-β1 expression.

The values from the various calcium-treated and 1,25-dihydroxy-vitamin D$_3$-treated mice were compared. When calcium was removed from the diet, the incidence of EAE was reduced 20% in both males and females. The lower the dietary level of calcium, the higher the dose of 1,25-dihydroxy vitamin D$_3$ required to prevent the symptoms. Thus, 1,25-dihydroxy vitamin D$_3$ is most effective in mice fed a diet adequate or high in calcium.

1,25-dihydroxyvitamin D$_3$ treatment of mice fed high dietary calcium caused decreased total numbers of lymphocytes in the lymph nodes, and increased interleukin (IL)-4 and transforming growth factor (TGF)-β1 mRNA expression. If calcium was omitted from the diet, 1,25-dihydroxyvitamin D$_3$ treatments increased TGF-β1 mRNA. Increased IL-4 mRNA and decreased lymphocytes in the lymph nodes only occurred in mice fed calcium and 1,25-dihydroxyvitamin D$_3$.

Our results demonstrate that dietary calcium and 1,25-dihydroxy-vitamin D$_3$ are both involved in development and in prevention of symptomatic EAE.

Human multiple sclerosis is most prevalent in females (Grossman, et al., 1991), while incidence and severity of EAE in mice differs in males vs. females, depending on strain (Cantorna, et al., 1996, Cua, et al., 1995). Thus, it is already known that gender is a major factor in this disease.

The current study was also designed to determine if 1,25-$(OH)_2D_3$ is equally effective in both sexes and if dietary calcium level plays any role in the development of the disease and the response to 1,25-$(OH)_2D_3$.

Our results indicate that both 1,25-$(OH)_2D_3$ and calcium regulate the immune response and that 1,25-$(OH)_2D_3$ is more effective against EAE in subjects, especially females, fed adequate or high dietary calcium levels.

Materials and Methods

Animals and Diets. The B10.PL mice were produced in our colony using breeding pairs obtained from Jackson Laboratories (Bar Harbor, Me.). During breeding, the mice were fed Purina diet 5008 Formilab (Richmond, Ind.), containing 100 IU/g of cholecalciferol (vitamin $D_3$). Mice were used for experiments at 6–8 wk of age at which time the females were 18–22 g and the males were 22–26 g. For experiments, all of the mice were fed synthetic diets (Yang, et al., 1993; Smith, et al., 1987) with the modifications described below. For all experiments each mouse was fed 4 g of the experimental diet (completely eaten) and the diets were replaced every 2–3 days for the duration of each experiment. Mice were fed 4 g of diet daily in order to insure that each mouse received its daily dose of 1,25-$(OH)_2D_3$ and that controls did not eat more than the 1,25-$(OH)_2D_3$ treated mice. Although the experimental diet was devoid of vitamin D, the mice were exposed to normal light and, therefore, were not vitamin D deficient. EAE was induced in all mice one week after the experimental diets were started. For mice with severe symptoms of EAE, food was placed in small dishes on the bottom of the cage. At the end of the experiments, mice were weighed, killed, and bled.

In the first experimental design, male and female mice were fed diets which contained 1 g calcium/100 g diet and EAE was induced. In a second series of experiments groups of 8–12 mice were fed the experimental diet (control treatment) without vitamin D or the experimental diet plus various concentrations of 1,25-$(OH)_2D_3$ as indicated. Females were fed 1,25-$(OH)_2D_3$ ranging from 0 to 200 ng/d and the males were fed 0 to 800 ng/d. The experimental diet contained one of 3 calcium concentrations; 20 mg (low), 470 mg (medium) or 1 g (high) calcium/100 g diet as indicated. The final experimental design used only male which were fed the control diet or the same diet containing 100 ng 1,25-$(OH)_2D_3$/daily. These mice were fed diets, which contained low, medium, or high calcium as indicated. This feeding protocol resulted in 6 groups of 6–8 male mice each. This dose of 1,25-$(OH)_2D_3$ was chosen because it completely prevented EAE in male mice fed high calcium diets. All of the procedures described were reviewed and approved by the University of Wisconsin-Madison Research Animal Resources Center Committee Review Board on Sep. 9, 1994 and the protocol number is A-07-3000-A00755-4-08-94.

EAE disease induction. Myelin basic protein (MBP) was isolated from guinea pig spinal cords (Cantorna, et al., 1996). MBP was lyophilized and stored at −20° C. For immunizations, MBP was dissolved in 0.1 mol/L acetic acid at a concentration of 8 g/L (Cantorna, et al., 1996). Ether anesthetized mice were immunized subcutaneously with 0.1 ml of MBP (400 mg/mouse) emulsified in an equal volume of Complete Freund's Adjuvant (CFA, Difco Laboratories, Detroit, Mich.) containing *Mycobacterium tuberculosis* H37 Ra. In addition, on the day of immunization and two days later mice were injected i.p. with 200 ng of pertussis toxin (LIST Biological Laboratories, Campbell, Calif.) suspended in sterile saline. This immunization protocol resulted in the induction of EAE in 80–100% of the mice. Male mice were killed on d 21 post-immunization to measure various immune responses. The EAE scoring system was: 0=normal; 1=limp tail; 2=paraparesis with a clumsy gait; 3=hind limb paralysis; 4=hind and fore limb paralysis; 5=moribund.

Lymphocytes. Axillary, brachial and inguinal lymph nodes (LN) from 6 mice were collected and pooled from control and 1,25-$(OH)_2D_3$ treated mice on d 21 post-immunization. Each experiment was repeated 3 times in its entirety. These LNs were chosen because they drained the site of immunization. Collected LN were disrupted manually using a 23 g needle and a pair of forceps. Total cell numbers in the LN were determined by counting the number of lymphocytes from control- and 1,25-$(OH)_2D_3$ treated mice and dividing by the number of mice in the group. Flow cytometry of fluorescent-labeled cell populations (Thy-1, class II, CD4 and CD8) were done on LN cells from control- and 1,25-$(OH)_2D_3$-treated mice using standard protocols and exactly as described (Smith, et al., 1987). For cytokine PCR analysis, LN cells were saved for total cellular RNA isolation.

Transcript analysis by quantitative competitive PCR. Cells for mRNA analysis were dissolved in acid guanidinium thiocyanate, and total RNA was isolated by the phenol chloroform extraction method (Chomczynski and Sacchi, 1987). Total cellular RNA was reverse-transcribed using oligo dT primers according to the manufacturer's protocols (Promega) and quantitated by competitive PCR. Primers and mimic DNA specific for glyceraldehyde-3-phosphate dehydrogenase (G3PDH), IL-4 and TGF-$\beta$1 were obtained from Clontech Laboratories, Inc. (Palo Alto, Calif.) (Siebert and Larrick, 1992; Siebert and Larrick, 1993). Competitive cDNA mimics which included the G3PDH, IL-4 and TGF-$\beta$1 primer sequences adjoining a neutral DNA segment, were serially diluted and added to test cDNA aliquots (Siebert and Larrick, 1992; Siebert and Larrick, 1993). The authentic product to mimic bp sizes were 983/600 for G3PDH, 306/544 for IL-4, and 525/390 for TGF-$\beta$1. The mixture was amplified under predetermined optimal conditions and the products were resolved by 1.5% agarose gel electrophoresis and ethidium bromide stained. The cytokine bands were identified by size with respect to molecular weight standards. The mimic DNA dilution that yielded a band with a fluorescence intensity that matched the cytokine band was used to calculate cytokine cDNA copy number. The G3PDH transcript quantitation served as a control for reverse transcription efficiency. Values are reported as cytokine cDNA copies per 1000 copies of G3PDH cDNA.

Serum calcium and 1,25-$(OH)_2D_3$ analysis. After 50 days the mice were killed, blood was collected by heart puncture and serum was collected following clot formation. Serum calcium concentrations were determined using a Perkin Elmer atomic absorption spectrometer exactly as described (Mohamed, et al., 1995). 1,25-$(OH)_2D_3$ analysis was done exactly as described (Arbour, et al., 1996).

Statistics. Where possible, values reported were averages from multiple mice or experiments. Because of the variability in EAE induction, peak severity, and cytokine gene expression from one experiment to another, some values (FIG. 6) were reported as the values from one representative of three experiments. A two-sample test for binomial proportions was used for statistical analysis of all percent values as described (Rosner, 1986). Again where possible statistical analyses were done using a statistics program for the Macintosh (STATVIEW STUDENT). The unpaired two-group Student's t test (and confirmed using the Mann-Whitney U test) was done and values of $p<0.05$ were considered significant.

Results

Figure 1:
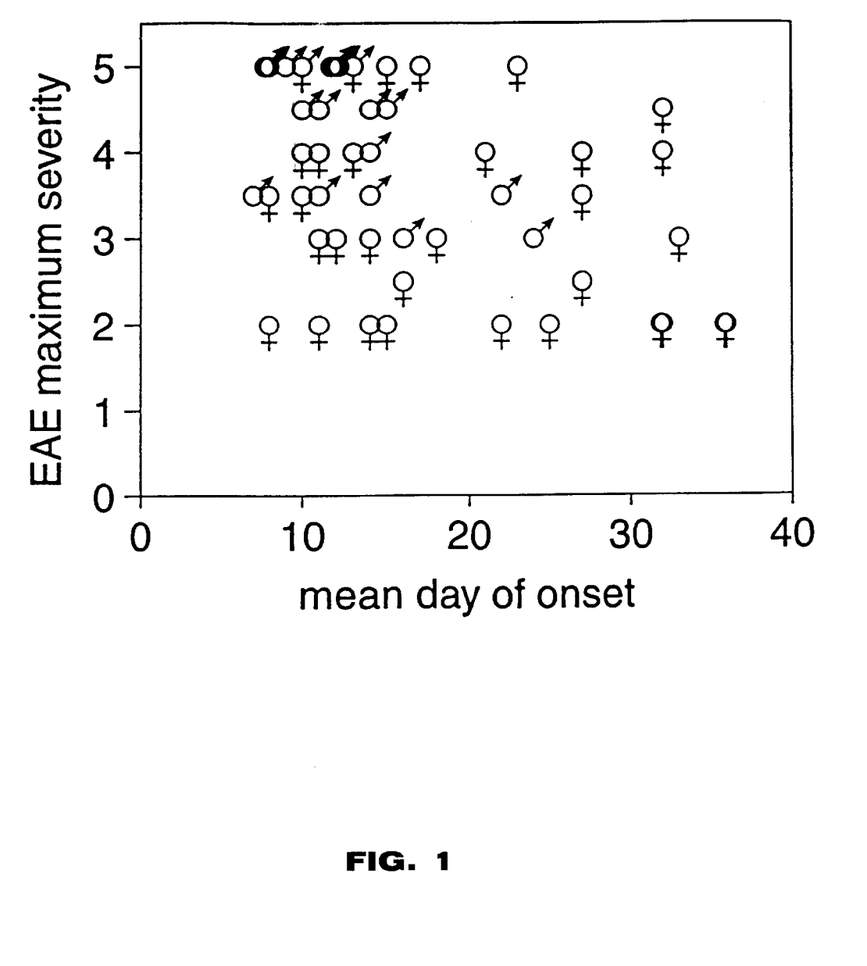
FIG. 1 is a graph of the incidence and severity of EAE in male and female B10.PL mice.

Sex and the development of EAE in B10.PL mice. When dietary calcium was high, the incidence of EAE was 98% for males and 96% for females. Males and females that did not develop EAE by day 50 post-immunization were excluded from the study. For mice that did develop EAE, the EAE maximum severity was plotted versus the day of EAE onset (FIG. 1). FIG. 1 is a graph of the incidence and severity of EAE in male and female B10.PL mice. Males developed EAE earlier and more severely than female B10.PL mice. 34% of female mice develop EAE after 24 days of immunization, while 100% of males develop EAE by this time ($p \leq 0.0002$). Each symbol represents an individual mouse. Females n=31, and males n=20.

The maximum EAE severity in the males ranged from 3 to 5. The maximum EAE severity in the females ranged from 2 to 5. Forty-seven percent of the males reached EAE scores of 5, while only 17% of females scored a 5 ($p0.03$). The day of EAE onset was also earlier for males (9–24 days) than females (9–38 days) ($p0.0002$). Thirty-four percent of the females developed EAE 24 days after immunization. Male mice were more susceptible to EAE then female mice.

Dietary calcium and the incidence of EAE. EAE disease severity was unaffected by changes in dietary calcium. Instead, the incidence of EAE varied with the amount of dietary calcium. Diets containing high calcium resulted in EAE incidence values approaching 100% (FIG. 2).

Figure 2:
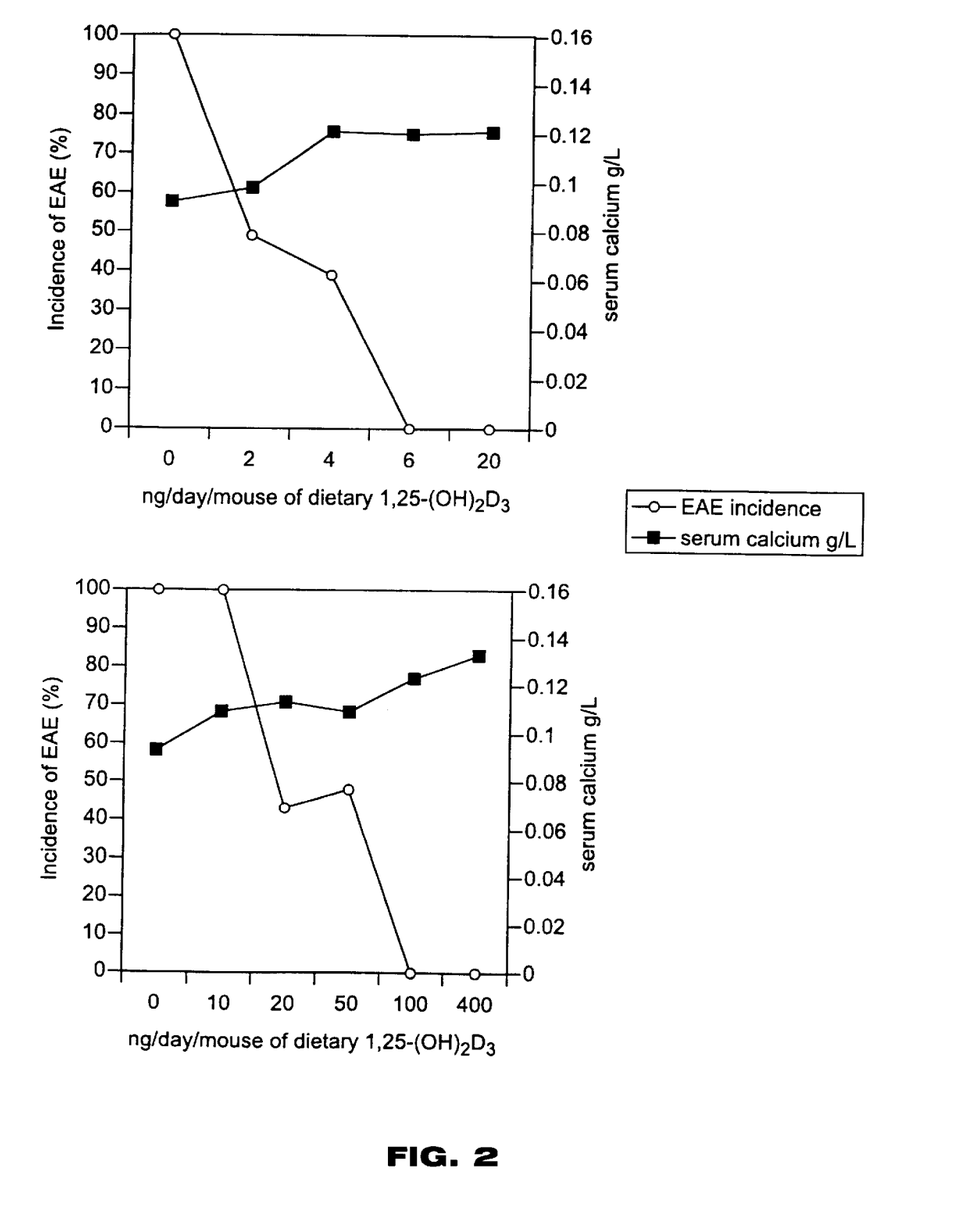
FIG. 2 is a graph of the $1,25\text{-}(OH)_2D_3$ dose response of male and female mice fed diets that contain 1 g calcium/100 g diet.
Figure 3:
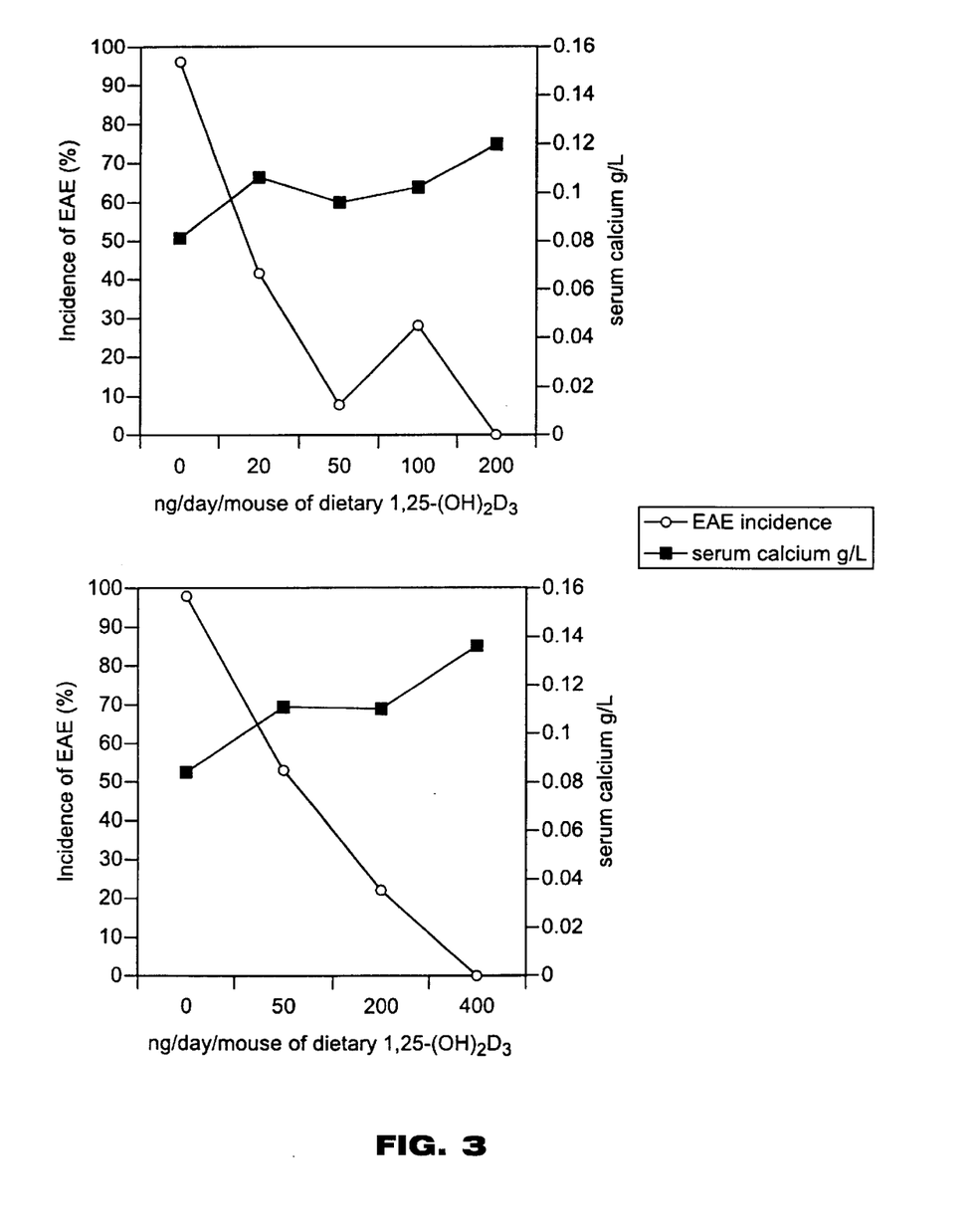
FIG. 3 is a graph of the $1,25\text{-}(OH)_2D_3$ dose response of males and females fed diets that contain 470 mg calcium/100 g diet.
Figure 4:
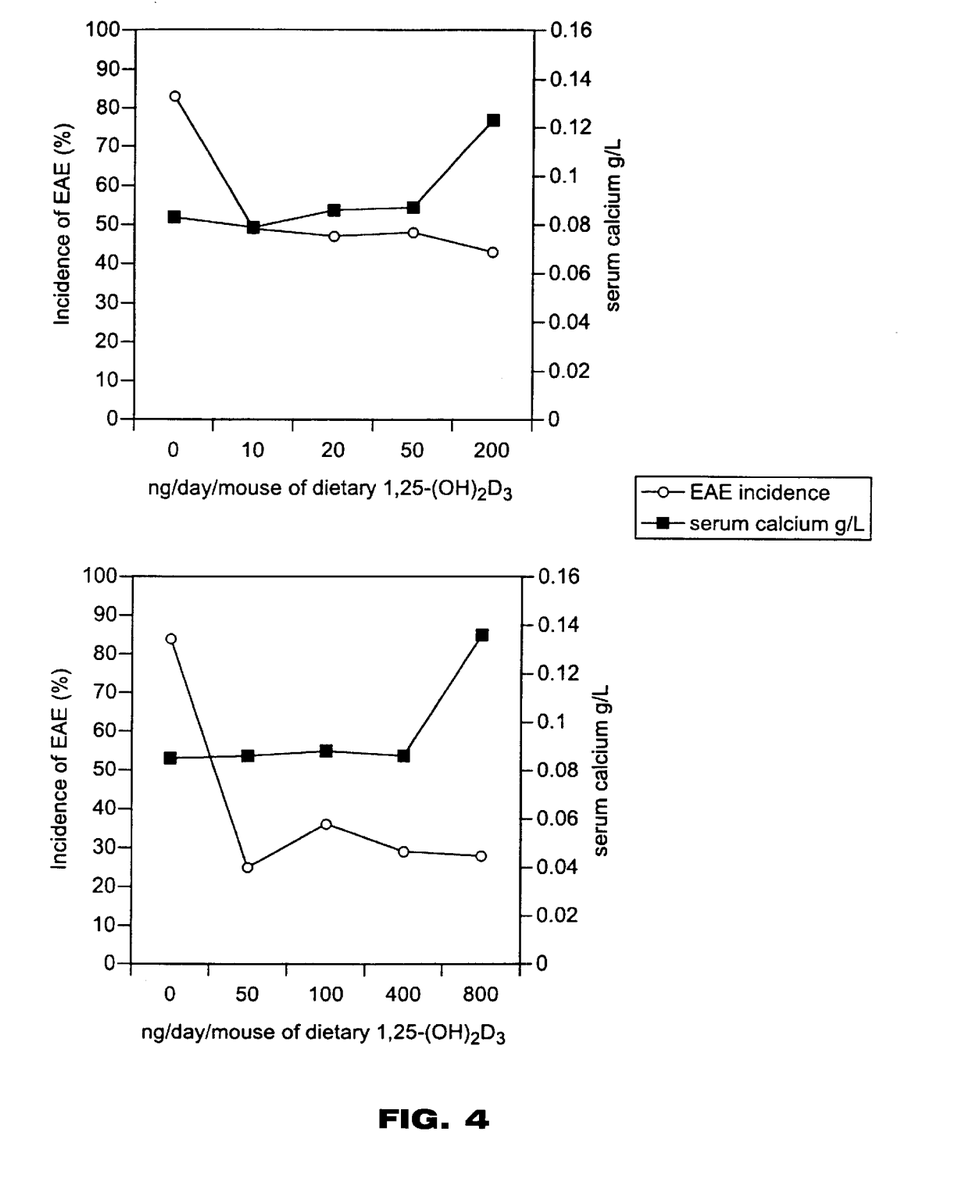
FIG. 4 is a graph of the $1,25\text{-}(OH)_2D_3$ dose response of males and females fed diets that contain 20 mg calcium/100 g diet.

FIG. 2 is a graph of the 1,25-$(OH)_2D_3$ dose response of male and female mice fed diets that contain 1 g calcium/100 g diet. The incidence of EAE in mice fed diets high in calcium was 100% for males and 99% for females. EAE was completely prevented in females at 6 ng/d of 1,25-$(OH)_2D_3$ top and in males at 100 ng/d of 1,25-$(OH)_2D_3$ bottom. Each data point represents at least 6 and as many as 32 mice. "*" indicates significantly different values compared to mice fed no 1,25-$(OH)_2D_3$ $p<0.05$. Males and females fed low calcium diets had EAE incidences around 82–83% (FIGS. 2–4). The EAE incidence of both male ($p0.07$) and female ($p0.08$) mice fed low calcium diets was lower (although not significantly lower) than mice on high calcium. It is well-documented that low dietary calcium stimulates the production of 1,25-$(OH)_2D_3$ (DeLuca 1983). Plasma 1,25-$(OH)_2D_3$ values of mice on high calcium diets ranged from 0.06–0.18 $\mu$mol/L of serum and values of mice fed low calcium ranged from 0.10–0.36 $\mu$mol/L of serum. FIG. 3 is a graph of the 1,25-$(OH)_2D_3$ dose response of males and females fed diets that contain 470 mg calcium/100 g diet. The incidence of EAE in mice fed medium calcium containing diets was 98% in males and 96% in females. EAE was completely prevented in females at 200 ng/d of 1,25-$(OH)_2D_3$ top and in males at 400 ng/d of 1,25-$(OH)_2D_3$ bottom. Each data point represents at least 6 and as many as 25 mice. *Significantly different then values of mice fed no 1,25-$(OH)_2D_3$ $p<0.05$.

A median dietary calcium level resulted in an intermediate EAE incidence of 95–99% (FIG. 3).

Mice fed low calcium diets and treated with 1,25-$(OH)_2D_3$ showed a significant (males $p<0.007$ and females $p<0.05$) drop in EAE incidence of 40–45% compared to mice who were not treated with 1,25-$(OH)_2D_3$ (FIG. 4). FIG. 4 is a graph of the 1,25-$(OH)_2D_3$ dose response of males and females fed diets that contain 20 mg calcium/100 g diet. The incidence of EAE in mice fed diets containing low calcium was 83% in males and 82% in females. EAE was never completely prevented in females at 200 ng/d of 1,25-$(OH)_2D_3$ top or in males at 800 ng/d of 1,25-$(OH)_2D_3$ bottom. Lower doses of 1,25-$(OH)_2D_3$ decreased the incidence of EAE to 30% ($p \leq 0.007$) in males and 45% ($p \leq 0.05$) in females without raising serum calcium. Each data point represents at least 8 and as many as 22 mice. "*" indicates significantly different values compared to mice fed no 1,25-$(OH)_2D_3$ $p<0.05$. The 40–45% decrease in EAE incidence occurred in the absence of an increase in serum calcium concentrations (0.0022±0.002 mmol/L, FIG. 4).

1,25-$(OH)_2D_3$, serum calcium and the prevention of EAE. When dietary calcium was high, 6 ng/d of 1,25-$(OH)_2D_3$ prevented EAE in females and 100 ng/d of 1,25-$(OH)_2D_3$ was needed for males (FIG. 2). At these doses of 1,25-$(OH)_2D_3$, serum calcium was elevated. At a medium dietary calcium level, 200 ng/d of 1,25-$(OH)_2D_3$ in females and 400 ng/d in males were needed to prevent EAE (FIG. 3). When calcium in the diet was low, EAE was not prevented by even high doses of 1,25-$(OH)_2D_3$. These doses of 1,25-$(OH)_2D_3$ raised calcium significantly from 0.0020±0.0001 to 0.0032±0.0002 mmol/L calcium (FIG. 4). At all levels of dietary calcium, sustained hypercalcemia was associated with significant weight loss (Table 1). Finally, at least 4 times more 1,25-$(OH)_2D_3$, and at high calcium intakes, 17 times more 1,25-$(OH)_2D_3$ was needed to prevent EAE in males than females. For the 1,25-$(OH)_2D3$ treated mice the overall symptoms of EAE (day of onset, paralysis scores) decreased as the incidence dropped (data not shown).

1,25-$(OH)_2D_3$, serum calcium and the immune response. 1,25-$(OH)_2D_3$ treatment of mice on high calcium diets resulted in a net loss of lymphocytes and the increased expression of IL-4 and TGF-$\beta$1 (Cantorna, et al., 1998b). Control mice with EAE had $3.5-4.1 \times 10^7$ cells in the LN regardless of the amount of calcium in their diets (FIG. 5).

Figure 5:
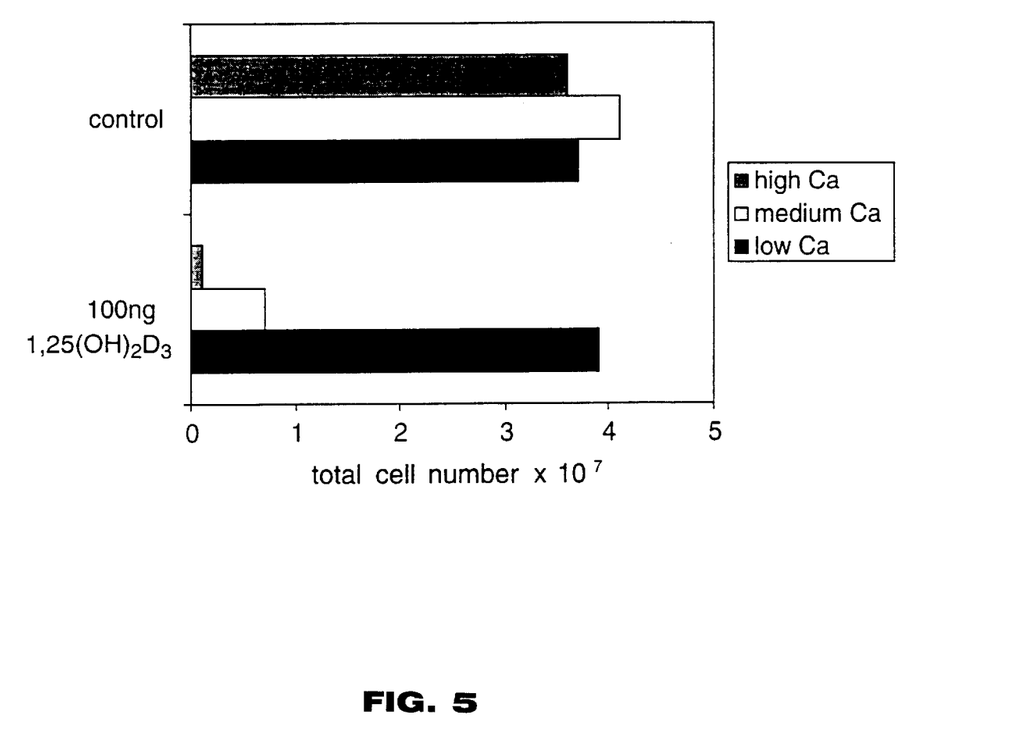
FIG. 5 is a bar graph of the effect of $1,25\text{-}(OH)_2D_3$ and calcium on the total cells recoverable from the draining LN of mice three weeks after EAE induction.

FIG. 5 is a bar graph of the effect of 1,25-$(OH)_2D_3$ and calcium on the total cells recoverable from the draining LN of mice three weeks after EAE induction. Groups of male B10.PL mice were fed low, medium, and high calcium diets with or without the addition of 100 ng 1,25-$(OH)_2D_3$ and EAE was induced. The experiment was repeated three times with six mice per group. Values are mean±the SE of the values from 3 experiments. "*" indicates significantly different values compared to values of mice not treated with 1,25-$(OH)_2D_3$ $p<0.05$.

The total number of cells in the LN of 1,25-$(OH)_2D_3$ treated mice with EAE was the same as controls fed low calcium diets but decreased dramatically ($p \leq 0.001$) with the addition of calcium to the diet (FIG. 5). Cell surface analysis showed that regardless of dietary calcium or 1,25-$(OH)_2D_3$ treatment Thy-1 positive cells made up 52–57% of the LN, CD4+ cells were 40–44% of the LN, and CD8+ cells were 18–21% of the LN. There was no effect of 1,25-$(OH)_2D_3$ or calcium treatment on G3PDH mRNA expression and therefore the IL-4 and TGF-$\beta$1 mRNA levels reflect the IL-4 and TGF-$\beta$1 levels per cell in the LN. Little IL-4 was detected in the LN of control fed mice with EAE regardless of the amount of calcium in the diet (FIG. 6).

Figure 6:
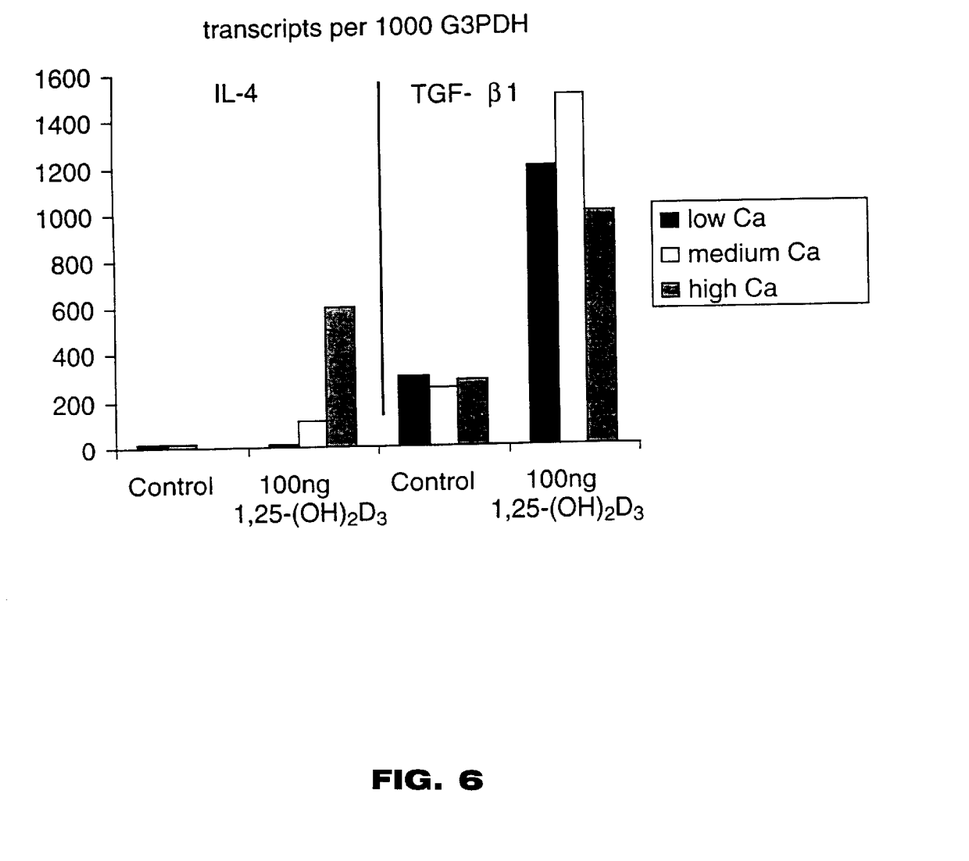
FIG. 6 is a bar graph of the effect of $1,25\text{-}(OH)_2D_3$ and calcium on the IL-4 and TGF-β1 transcripts in the LN.

FIG. 6 is a bar graph of the effect of 1,25-$(OH)_2D_3$ and calcium on the IL-4 and TGF-$\beta$1 transcripts in the LN. Groups of male B10.PL mice were fed low, medium, and high calcium with or without the addition of 100 ng 1,25-$(OH)_2D_3$ and EAE was induced. There was no effect of 1,25-$(OH)_2D_3$ or calcium diets on G3PDH expression. One representative experiment of 3 is presented. Each value represents the results from 6 pooled mice. Although the overall magnitude of the response varied from experiment to experiment, these were highly reproducible results.

IL4 production in 1,25-$(OH)_2D_3$ fed mice was not different from controls when they were fed low calcium diets. The amount of IL-4 produced increased as the calcium in the diet increased but only in cells from mice treated with 1,25-(OH)

$_2D_3$ (FIG. 6). TGF-β1 levels in the LN of control fed mice were uniformly low compared to those in mice given 1,25-$(OH)_2D_3$ (FIG. 6). Dietary calcium had no effect on TGF-β1 expression (FIG. 6). For IL-4 mRNA expression, mice with the fewest cells in the LN (high calcium plus 1,25-$(OH)_2D_3$ treated) expressed the most IL-4. For TGF-β1 mRNA expression, all mice treated with 1,25-$(OH)_2D_3$ expressed high levels of TGF-β1 regardless of the number of cells in the LN.

Discussion

The effects of dietary calcium and 1,25-$(OH)_2D_3$ are critically linked for the prevention of EAE in mice. When mice are fed a diet containing high calcium (approaching that found in nonpurified diets), 1,25-$(OH)_2D_3$ at appropriate doses is 100% effective in preventing EAE. In contrast, if calcium is removed from the diet, 1,25-$(OH)_2D3$ reduced the incidence of EAE by only 50%. When an intermediary level of calcium is fed, the effectiveness of 1,25-$(OH)_2D_3$ is intermediate between low calcium and a high calcium diet. These results argue strongly that calcium is involved in the action of 1,25-$(OH)_2D_3$ in the prevention and treatment of this autoimmune disease (Holda and Swanborg, 1982; Powell, et al., 1990).

It is of some interest that in mice given a low calcium diet, doses of 1,25-$(OH)_2D_3$ that nevertheless produce frank hypercalcemia, show little or no further reduction in the incidence of EAE. Thus, in the absence of a dietary source of calcium 1,25-$(OH)_2D_3$ mediated increases in serum calcium are ineffective for the further suppression of EAE. On the other hand, there are doses of 1,25-$(OH)_2D_3$ that do not cause hypercalcemia but that nevertheless reduce the incidence of EAE. Overall, our results argue that the 1,25-$(OH)_2D_3$ may function by both calcium dependent and calcium independent mechanisms to suppress EAE.

Manipulating only dietary calcium had no effect on the immune response to EAE. The total cell number in the LN of mice with EAE was inversely related to the amount of dietary calcium fed in the 1,25-$(OH)_2D_3$ treated mice. Similarly, thymic atrophy resulted as a consequence of 1,25-$(OH)_2D_3$ induced hypercalcemia (Mohamed, et al., 1996). The decreased cell number in the LN may be due to 1,25-$(OH)_2D_3$ induced decreases in cell expansion or increases in cell death. IL-4 was increased, but not TGF-β1, elative to the amount of calcium fed. In the absence of added dietary calcium, 1,25-$(OH)_2D_3$ had no effect on IL-4 expression. 1,25-$(OH)_2D_3$ and calcium may actually be selectively inhibiting the differentiation and/or expression of cells that do not make IL-4. The result would seem to be an increase in IL-4 expression. Therefore, it is possible that IL-4 expression has not changed but instead the proportion of cells making IL-4 has increased. Conversely, TGF-β1 increased in response to 1,25-$(OH)_2D_3$ regardless of dietary calcium. This finding is consistent with our previous work suggesting TGF-β1 gene expression is directly regulated by 1,25-(OH)$_2D_3$ (Cantorna, et al., 1998b). Calcium is an important intracellular messenger, but how dietary calcium might affect intracellular calcium is unknown. More work is needed to understand the relationship of 1,25-$(OH)_2D_3$ and calcium as immune system regulators.

We note that low dietary calcium reduces the incidence of EAE, while at the same time it reduces the effectiveness of 1,25-$(OH)_2D_3$ in preventing EAE. The animals used in these experiments are not vitamin D depleted and thus contain stores of vitamin D and 25-hydroxyvitamin D. It is well known that low dietary calcium markedly stimulates the production of 1,25-$(OH)_2D_3$ (DeLuca, 1983). This endogenously produced hormone may well play a role in reducing the incidence of EAE. On the other hand, it is clear that even large doses of 1,25-$(OH)_2D_3$ cannot completely prevent EAE in these mice. Low dietary calcium must, therefore, play more than one role.

TABLE 1

Serum calcium and weight of male mice fed various levels of calcium and 100 ng/d 1,25-$(OH)_2D_3$.

| Dietary Calcium → | 20 mg/100 g | | 470 mg/100 g | | 1 g/100 g | |
|---|---|---|---|---|---|---|
| 1,25-$(OH)_2D$ ↓ | Weight[3] (g) | Serum Calcium (mmol/L) | Weight (g) | Serum Calcium (mmol/L) | Weight (g) | Serum Calcium (mmol/l) |
| none | 23 ± 2 | 0.0020 ± 0.0001 | 26 ± 1 | 0.0021 ± 0.0001 | 26 ± 3 | 0.0023 ± 0.0001 |
| Intermediate[2] | 27 ± 2 | 0.0021 ± 0.0001 | 23 ± 2 | 0.0028 ± 0.0001 | 25 ± 2 | 0.0030 ± 0.0000* |
| High | 13 ± 3* | 0.0032 ± 0.0001* | 17 ± 3* | 0.0035 ± 0.0002* | 15 ± 1* | 0.0035 ± 0.0002* |

[1]Values are mean ± SD of 6–34 mice.
[2]Intermediate doses of 1,25-$(OH)_2D_3$ were 40–500 ng/d fed 20 mg/100 g dietary calcium, 50–200 ng/d fed 470 mg/100 g dietary calcium and 10–50 ng/d fed 1 g/100 g dietary calcium. High doses of 1,25-$(OH)_2D_3$ were 800 ng/day on 20 mg/100 g dietary calcium, 400 ng/day on 470 mg/100 g dietary calcium and 100–400 ng/day on 1 g/100 g dietary calcium.
[3]Mice were weighted at the end of the 50 d experiment. Starting weight was 22–26 g.
*Significantly less (for weight) and significantly higher (for calcium) than mice fed no 1,25-$(OH)_2D_3$ and the equivalent amount of dietary calcium.

REFERENCES

Arbour, N. C., Ross, T. K., Zierold, C., Prahl, J. M. and DeLuca, H. F., "A highly sensitive method for large-scale measurements of 1,25-dihydroxyvitamin D," *Anal. Biochem.* 255:148–154, 1988.

Bhalla, A. K., Anesto, E. P., Clemens, T. L., Holick, M. F. and Krane, S. M., "Specific high-affinity receptors for 1,25-dihydroxyvitamin $D_3$ in human peripheral blood mononuclear cells: Presence in monocytes and induction in T-lymphocytes following activation," *J. Clin. Endocrinol. Metab.* 57:1308–1310,1983.

Bouillon, R., Okamura, W. H. and Norman, A. W., "Structure-function relationships in the vitamin D endocrine system," *Endocrine Rev.* 16:200–230, 1995.

Cantorna, M. T., Hayes, C. E. and DeLuca, H. F., "1,25-Dihydroxyvitamin $D_3$ reversibly blocks the progression of relapsing encephalomyelitis," *Proc. Natl. Acad. Sci. USA* 93:7861–7864, 1996.

Cantorna, M. T., Hayes, C. E. and DeLuca, H. F., "1,25-Dihydroxycholecalciferol inhibits the progression of arthritis in murine models of human arthritis." *J. Nutr.* 128:68–72, 1998a.

Cantorna, M. T., Woodward, W. T., Hayes, C. E. and DeLuca, H. F., "1,25-dihydroxyvitamin $D_3$ is a positive regulator for the two anti-encephalitogenic cytokines TGF-β1 and IL-4," *J. Immunol.* 160:5314–5319, 1998b.

Chomczynski, P. and Sacchi, N., "Single-step method of RNA isolation by acid guanidinium thiocyanate-phenol-chloroform extraction," *Anal. Biochem.* 162:156, 1987.

Cua, D. J., Hinton, D. R. and Stohlman, S. A., "Self-antigen-induced Th2 responses in experimental llergic encephalomyelitis (EAE)-resistant mice," *J. Immunol.* 155:4052–4059, 1995.

DeLuca, H. F., "The vitamin D-calcium axis," In: *Calcium in Biological Systems* (Rubin, R. P., Weiss, G. B., & Putney, J. W., Jr., eds.), pp. 491–511, 1983.

DeLuca, H. F., "The genetics and biology of vitamin D," In: *Principles of Medical Biology* (E. E. Bittar and N. Bittar, eds.), Greenwich, Conn., JAI Press, Inc., pp. 617–641, 1997.

Grossman, C. J., Roselle, G. A. and Mendenhall, C. L., "Sex steroid regulation of autoimmunity, " *J. Steroid Biochem. Molec. Biol.* 40:649–659, 1991.

Hullett, D. A., Cantorna, M. T., Redaelli, C., Clagett-Dame, M., Hayes, C. E., McCary, L., Humpal-Winter, J., Sollinger, H. W. and DeLuca, H. F., "Prolongation of allograft survival by 1,25-dihydroxyvitamin $D_3$," *Transplantation* 66:824–828, 1998.

Lemire, J. M. and Archer, D. C., "1,25-Dihydroxyvitamin $D_3$ prevents the in vivo induction of murine experimental autoimmune encephalomyelitis," *J. Clin. Invest.* 87:1103–1107, 1991.

Mohamed, M. I., Beckman, M. J., Meehan, J. and DeLuca, H. F., "Effect of 1,25-dihydroxyvitamin D3 on mouse thymus: role of extracellular calcium," *Biochim. Biophys. Acta.* 1289:275–283, 1996.

Pike, J. W., "Vitamin $D_3$ receptors: Structure and function in transcription," *Ann. Rev. Nutr.* 11:189–216, 1991.

Provvedini, D. M., Tsoukas, D. C., Deftos, L. J. and Manolagas S. C., "1,25-Dihydroxyvitamin $D_3$ receptor in human leukocytes," *Science* 221:1181–1183, 1983.

Rosner, B., "Hypothesis Testing: Categorical Data In: Fundamentals of Biostatistics," $2^{nd}$ ed. (Payne M. ed.) Boston, Duxbury Press, pp. 302–317, 1986.

Ross, T. K., Darwish, H. M. and DeLuca, H. F., "Molecular biology of vitamin D action," In: *Vitamins and Hormones* (G. Litwack ed.), San Diego: Academic Press, pp. 281–326,1994.

Siebert, P. D. and Larrick, J. W., "Competitive PCR," *Nature* 359:557–558, 1992.

Siebert, P. D. and Larrick, J. W., "PCR MIMICS: Competitive DNA fragments for use as internal standards in quantitative PCR," *BioTechniques* 14:244–249, 1993.

Smith, S. M., Levy, N. S. and Hayes, C. E., "Impaired immunity in vitamin A deficient mice," *J. Nutr.* 117:857–865,1987.

Yang, S., Smith, C., Prahl, J. and. & DeLuca, H. F., "Vitamin D deficiency suppresses cell-mediated immunity in vivo," *Arch. Biochem. Biophys.* 303:98–106, 1993.

We claim:

1. A method of treating multiple sclerosis patients, comprising the step of administering an amount of calcium supplement and an amount of a vitamin D compound effective to diminish multiple sclerosis symptoms, wherein the amount of calcium and vitamin D compound are synergistic effective amounts, wherein the calcium is in the form of calcium carbonate and the vitamin D compound is 1,25-dihydroxyvitamin $D_3$.

2. A pharmaceutical composition comprising an amount of calcium and vitamin D compound, wherein the amount of calcium and vitamin D compound are synergistic effective amounts for the treatment of multiple sclerosis, wherein calcium is in the form of calcium carbonate and the vitamin D compound is 1,25-dihydroxyvitamin $D_3$.

* * * * *

UNITED STATES PATENT AND TRADEMARK OFFICE
CERTIFICATE OF CORRECTION

PATENT NO. : 6,479,474 B2
DATED : November 12, 2002
INVENTOR(S) : Hector F. DeLuca et al.

It is certified that error appears in the above-identified patent and that said Letters Patent is hereby corrected as shown below:

Title page,
Item [75], Inventors, "Margherite T. Cantorna" should read
-- Margherita T. Cantorna --.

Signed and Sealed this

Twenty-first Day of June, 2005

JON W. DUDAS
*Director of the United States Patent and Trademark Office*